United States Patent
Kéri et al.

(10) Patent No.: US 6,812,007 B1
(45) Date of Patent: Nov. 2, 2004

(54) PROCESS FOR THE ISOLATION AND PURIFICATION OF MEVINOLIN

(76) Inventors: Vilmos Kéri, Kemény Zs. 7, H-4028 Debrecen (HU); Irma Högye, Egyetem 10, H-4027 Debrecen (HU); Antónia Jekkel, Damjanich 38, H-1071 Budapest (HU); Ilona Bagdi, Kurucz 71, H-4025 Debrecen (HU); Gábor Ambrus, Csalán 45/B, H-1025 Budapest (HU); Attila Jakab, Sántha K. 10, H-4032 Debrecen (HU); Attila Andor, Pcrcs 4, H-1221 Budapest (HU); Lajos Deák, Lehel 20, H-4032 Debrecen (HU); István Szabó, Reile 14, H-6000 Kecskemét (HU); János Bálint, Péchy 5, H-4032 Debrecen (HU); Zsuzsanna Scheidl, Rózsa 51, H-1041 Budapest (HU); Etelka Deli, Jerikó 8., H-4032 Debrecen (HU); Gyula Horváth, Kigyó 4-6, H-1052 Budapest (HU); Csaba Szabó, Fáy A. 21, H-4026 Debrecen (HU); Ildikó Láng, Izabella 13, H-1077 Budapest (HU); Imre Székely, Gyergyó 11, H-4028 Debrecen (HU); Imre Moravcsik, Mester 38, H-1095 Budapest (HU); Vera Kovács, Civis 3, H-4032 Debrecen (HU); Szabolcs Mátyás, Mária 34, H-1085 Budapest (HU); Zsuzsanna Sztáray, Sumen 28, H-4024 Debrecen (HU); László Eszenyi, Bekecs 14, H-4030 Debrecen (HU); Éva Ilköy, Munkácsi 37, H-1046, Budapest (HU)

( * ) Notice: Subject to any disclaimer, the term of this patent is extended or adjusted under 35 U.S.C. 154(b) by 0 days.

(21) Appl. No.: 09/578,587

(22) Filed: Apr. 19, 2000

Related U.S. Application Data

(63) Continuation-in-part of application No. 08/659,961, filed on Jun. 7, 1996, now abandoned, which is a continuation of application No. 08/269,150, filed on Jun. 30, 1994, now abandoned, which is a continuation-in-part of application No. PCT/HU93/00051, filed on Sep. 8, 1993, now abandoned.

(30) Foreign Application Priority Data

Nov. 4, 1992 (HU) ............................................. 9203458

(51) Int. Cl.$^7$ ................................................ C12P 17/06
(52) U.S. Cl. ....................... 435/125; 435/117; 435/118; 435/170; 435/244; 435/115; 549/292
(58) Field of Search ................................ 435/125, 117, 435/113, 118, 170, 244; 549/911, 292

(56) References Cited

U.S. PATENT DOCUMENTS 5,403,728 A * 4/1995 Jekkel ........................ 435/125

FOREIGN PATENT DOCUMENTS

DE 3006216 * 4/1980
DE 302828 * 2/1981

OTHER PUBLICATIONS

Nakamura et al., J. Antibiotics, vol. 43, No. 12, pp. 1597–1600, 1990.*

* cited by examiner

Primary Examiner—Irene Marx
(74) Attorney, Agent, or Firm—Goodwin Procter LLP

(57) ABSTRACT

In a process for preparing mevinolin by fermentation of a biomass in a fermentation liquor, which includes dissolving mevinolin from the biomass into the fermentation liquor, and separating the biomass from the fermentation liquor to obtain a separated fermentation liquor, separating the mevinolin from the separated fermentation liquor, and recovering the end product, the improvement which comprises carrying out the dissolving at a pH between 7.5 and about 10, and the separating of the mevinolin is carried out at a pH between about 4.5 and about 1.

2 Claims, No Drawings

PROCESS FOR THE ISOLATION AND PURIFICATION OF MEVINOLIN

This is a continuation in part of application Ser. No. 08/659,961 filed on Jun. 7, 1996, now abandoned, which is a continuation of Ser. No. 08/269,150 filed on Jun. 30, 1994, now abandoned, which is a continuation-in-part of application Ser. No. PCT/HU/93/00051, filed on Sep. 8, 1993.

FIELD OF THE INVENTION

This invention relates to a process for the isolation and purification of mevinolin from fermentation liquor.

Mevinolin, also known as lovastatin, Mevacor, monacolin K, and MK 803 is a known antihypercholesteremic agent, which can be produced by fermentation using either a microorganism of the species *Aspergillus terreus* or different microorganism species of the Monascus genus, obtained either as an open chain hydroxy acid or as lactone. The compound has the formula

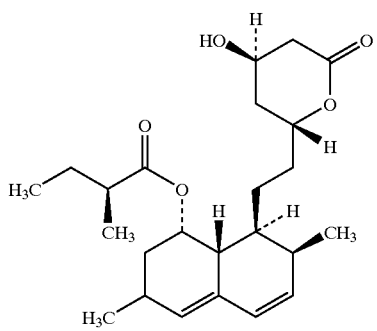

BACKGROUND OF THE INVENTION

The isolation of the active ingredient is suitably carried out either by directly extracting the fermentation liquor with a solvent, or by extracting the filtered liquor and the biomass and subsequently purifying the crude product such as by chromatography.

Ethyl acetate, chloroform or benzene can be used for the extraction. The fermentation liquor contains partly the open-chain hydroxy acid of mevinolin, 3,5-dihydroxy-7-[1,2,6,7,8,8a-hexahydro-2,6-dimethyl-8-(2-methylbutyryloxy)-naphthalene-1-yl]-heptanoic acid. This compound is heated in toluene to be lactonized to mevinolin. The purification of the mevinolin containing crude product completely in the lactone form can be carried out by chromatography and subsequent recrystallization in accordance with the process disclosed in U.S. Pat. No. 4,319,039.

In addition to extraction an $XAD_2$ adsorption resin can also be used for the isolation of mevinolin as disclosed in U.S. Pat. Nos. 4,231,938 and 4,319,039.

The main disadvantage of the extraction method is that together with the active ingredient the solvent also dissolves many other contaminants, and thus makes the further purification more complicated and expensive. Purification can be efficiently carried out by multistage column chromatography and subsequent recrystallization.

Experiments have been carried out to compare the extraction method described in Hungarian patent No. 187,296 to the method according to the present invention for the isolation of mevinolin from fermentation liquor obtained by cultivation of an *Aspergillus obscurus* MV-1 holotype strain (deposit No. NCAIM (P)F 001189 at the Hungarian National Collection) and other bacterial strains, such as *Aspergillus terreus*) accessible under ATCC 20542). The results, as shown in Example 1, demonstrate that the product obtained from the fermentation liquor by extraction cannot be properly purified by recrystallization. The preparation by this route of a product is not suitable for pharmaceutical purposes, therefore requires further purification by column chromatography.

DESCRIPTION OF THE INVENTION

The object of the present invention is to provide a process for the isolation of mevinolin from a fermentation liquor, which can be carried out more readily and more economically than the known processes, and which enables the preparation of the active ingredient in a quality suitable for pharmaceutical purposes.

The present invention is based on the recognition that the active ingredient can be separated with high efficiency directly from the filtered fermentation liquor at a pH between about 4.5 and about 1. The separated crude product does not need to be purified by chromatography, since only a surprisingly small amount of contamination separates together with it. Thus a simple recrystallization is sufficient to obtain a product of suitable quality.

According to the process of the present invention the active ingredient is dissolved from the biomass into the fermentation liquor at a pH of from about 7.5 to about 10. The biomass is filtered off, the crude product is separated from the filtered liquor at a pH of from about 4.5 to about 1 and purified by methods known per se, suitably by recrystallization.

The separation of the active ingredient has been investigated at different acidic pH values. The pH range of from about 1.8 to about 2.4, especially from about 2 to about 2.2 has been found to be the most suitable. It has also been found that the separation of the active ingredient from the filtered fermentation liquor, and especially the filterability of the precipitate, can be improved by the addition of bivalent or trivalent metal salts, for example earth alkali metal salts such as $CaCl_2$, $MgCl_2$, $MgSO_4$ or earth metal salts such as $Al_2(SO_4)_3$, or transition metal salts, such as ferrous, or ferric salts.

The active ingredient content of the filtered fermentation liquor is shown in the table below with the active ingredient having been filtered off at varying pH with or without adding calcium chloride to the filtered liquor. The active ingredient content was determined by high pressure liquid chromatography.

| | Active ingredient content of the filtered liquor ($\mu g/cm^3$) | |
|---|---|---|
| pH | without adding any salt | in the presence of 0.2M $CaCl_2$ |
| 7 | 418 | 60 |
| 6 | 387 | 65.8 |
| 5 | 201 | 103 |
| 4 | 58 | 50 |
| 3 | 31 | 22 |
| 2 | 14 | 10 |
| 1.5 | 10 | 10 |
| 1 | 8 | 8 |

As the majority of the active ingredient is bound to the biomass, both the efficiency of the dissolution into the fermentation liquor and the amount of the contaminants are of significance.

It has also been recognized that by carrying out the dissolution of the active ingredient into the fermentation liquor at a pH between about 7.5 and about 10, more particularly between about 8 and about 9, both the loss of the active substance and the amount of the contaminations can be kept at a minimum.

It was experimentally found that the dissolution of the active ingredient can be enhanced by adding a small amount of additives to the mixture. $C_{1-4}$ aliphatic alcohols, $C_{2-5}$ glycols, $C_{1-3}$ secondary or tertiary amines, $C_{1-5}$ alkyl acetates, dimethylformamide, polyethylene glycol, or polypropylene glycol have been found to be particularly suitable additives, and ethylene glycol and ethanol are most suitable additives.

The active ingredient content of the filtered fermentation liquor is shown in the following table before the separation of the active ingredient at about pH 9 and after the filtration thereof at about pH 2, both with and without additives.

| Additive | Active ingredient in filtered form liquor ($\mu$g/cm$^3$) | |
| --- | --- | --- |
| 1% vol. | @ pH 9 | @ pH 2 |
| diethylamine | 412 | 9.2 |
| triethylamine | 423 | 10.5 |
| dimethylformamide | 460 | 6.9 |
| methanol | 429 | 7.9 |
| ethanol | 455 | 11.2 |
| isopropanol | 467 | 8.7 |
| ethylene glycol | 467 | 5.1 |
| propylene glycol | 450 | 10.2 |
| polypropylene glycol | 369 | 19.1 |
| isobutyl acetate | 258 | 8.8 |
| polyethylene glycol | 431 | 11.8 |
| control (without additive) | 193 | 8.6 |

It is clear from the foregoing table that the active ingredient content of the filtered liquor is higher when additives are used than without the use of the additives. Thus the additives promote the dissolution of the active ingredient from the biomass into the fermentation liquor. It can also be seen that the additives do not have any influence on the separation because that can be accomplished with the same efficiency with or without the use of additives. Their use, is therefore suitable since they amplify the procedure, because a single forming of a suspension from the biomass is sufficient. On the other hand, when no additives are used then the procedure has to be repeated to achieve the same efficiency.

As shown in the next table, the additives perform well, even when employed at a small concentration, such as about 0.1% volume based on the fermentation liquor.

| concentration of ethanol | active ingredient content of the filtrate liquor ($\mu$g/cm$^3$) | |
| --- | --- | --- |
| % vol. | @ pH 9 | @ pH 2 |
| 0.1 | 400 | 8.9 |
| 0.5 | 425 | 8.5 |
| 1.0 | 455 | 11.2 |
| 5.0 | 447 | 11.5 |
| 10.0 | 441 | 13.0 |
| 15.0 | 434 | 18.1 |
| 20.0 | 430 | 26.0 |

The crude product can be purified by any suitable method, such as by recrystallization. Crystallization is suitably carried out from isobutyl acetate by washing the isobutyl acetate solution of the substance with a weakly basic 2.5% wt. ammonium sulfate solution adjusted to about 8.5 pH, the solvent phase is clarified with carbon, concentrated and the separated product is filtered off.

The present process enables elimination of the extraction of both the fermentation liquor and the biomass from the procedure, the active ingredient separated from the filtered fermentation liquor at acidic pH is surprisingly pure, and so it does not require to be purified by chromatography, but simple recrystallization leads to a product of acceptable pharmaceutical purity. Therefore the process is simple and can be economically accomplished with only a slight loss of substance, at yields above 90%.

The invention is further illustrated by the following examples.

EXAMPLE 1

A comparative experiment was carried out by using as comparison the extraction method specified in Hungarian patent No. 187,296.

800 g of fermentation liquor cultured by an *Aspergillus obscurus* MV-1 holotype strain, deposition access No. NCAIM (National Collection of Agricultural and Industrial Microorganisms) (P)F 001189) containing a total of 670 mg of mevinolin both as lactone and as hydroxy acid were adjusted to pH 4 with 20% wt sulfuric acid solution. The liquor was then extracted with 400 cm$^3$ of ethyl acetate. The organic phase containing the active ingredient was separated and the aqueous residue was extracted again with further 400 cm$^3$ of ethyl acetate. The ethyl acetate extracts were combined to yield 760 cm$^3$, containing 643 mg of the active ingredient, dried over anhydrous sodium sulfate and concentrated under vacuum. The concentrate was boiled in 100 cm$^3$ toluene for 2 hours. Then the undissolved particles were filtered off and washed successively with 50 cm$^3$ of 5% wt sodium hydrogen carbonate solution and 50 cm$^3$ of water. The toluene solution was dried over anhydrous sodium sulfate and evaporated under vacuum. The thus obtained 3.5 g oily product contained 630 mg of the active ingredient. The oily product was dissolved by warming in 15 cm$^3$ of ethanol and allowed to stand at a temperature of 5° C. for 24 hours. The product did not separate out in crystalline form. The solvent was then removed and the oily product (3.5 g) was divided into two parts.

1.75 g of product was attempted to be recrystallized from 6 cm$^3$ of isobutyl acetate as specified in Example 2. The product did not separate out in crystalline form.

The other part of the product was subjected to column chromatography using a 22 cm long column having a 1.6 cm diameter packed with 20 g of a silica gel sold under the trademark Kieselgel 60 having a particle size of from 0.063 to 0.2 mm. The column was eluted with a 40:60 mixture of ethyl acetate and methylene chloride at a rate of 20 cm³/hour. The 6 to 10 fractions containing the active ingredient were combined, clarified with activated carbon, filtered and evaporated under vacuum to yield 260 mg of yellowish white solid residue, which was recrystallized from ethanol. The separated crystals were filtered through a G-4 sieve, washed with 10 cm³ of n-hexane and dried under vacuum at room temperature. A first batch of 180 mg of chromatographically pure mevinolin were obtained.

The evaporation residue of the mother liquor obtained during the crystallization was recrystallized again from ethanol to obtain a second batch of 35 mg mevinolin. The quality of the second batch of product was the same as that of the first batch.

EXAMPLE 2

800 g of fermentation liquor cultured by the Aspergillus strain of Example 1 containing a total amount of 536 mg of mevinolin both as lactone and as hydroxy acid were diluted to 1200 g with water. Then the solution was kept at a pH between 8.5 and 9 with 20% wt potassium hydroxide solution under continuous stirring for 2 hours. The biomass was then filtered off and suspended twice each in 400 cm³ of water. The suspension was adjusted to a pH between 8.5 and 9 with 20% wt KOH solution, filtered again and the filtrates were combined. Thus 1900 cm³ of filtered liquor containing 530 mg of active ingredient was obtained. The liquor was then adjusted to pH 2.1 with 15% wt sulfuric acid solution, under stirring. The separated precipitate was settled, filtered, suspended in 100 cm³ sulfuric acid solution adjusted to pH 2 and filtered again. The active ingredient concentration of the filtrate was 12 $\mu$g/cm³.

The filtered aqueous precipitate was dissolved in 50 cm³ isobutyl acetate, the aqueous phase was separated and the solvent phase was concentrated to 2.5 cm³. The concentrate was dissolved in 60 cm³ of isobutyl acetate, washed twice each time with 60 cm³ of an aqueous ammonium sulfate solution adjusted to pH 8.5 with ammonium hydroxide, clarified with 0.5 g of activated carbon, concentrated to 10 cm³, allowed to crystallize for 24 hours at 5° C., filtered and dried under vacuum. 436 mg mevinolin were recovered. The active ingredient content was 98.7% by high pressure liquid chromatography. A further 65 mg of mevinolin were obtained form the combined mother liquors, with a purity of 92.8%. The crude products were combined and recrystallized from ethanol, to obtain 450 mg of product with an active ingredient content of 99.8% by high pressure liquid chromatography.

The end product contained 0.17% dihydromevinolin by gas chromatography $[\alpha]25_D=+329.8°$ (specific optical rotation) according to the method of 22 United States Pharmacopoeia p.3273 with 0.5 g of the material dissolved in 100 ml a acetonitrile.

EXAMPLE 3

800 g of fermentation liquor cultured by the Aspergillus strain of Example 1 containing a total amount of 605 mg of mevinolin both as lactone and as hydroxy acid were diluted to 1200 g with water. Then 2.4 g of ethylene glycol were added to the mixture, and kept at pH 8.5–9.0 by adding 20% wt KOH solution under continuous stirring for 2 hours. The biomass was then filtered off and suspended in 400 cm³ water containing 0.8 g of ethylene glycol. The suspension was adjusted to pH 8.5–9.0 with 20% wt KOH solution, filtered again and the filtrates were combined. 1470 cm³ of filtered liquor were obtained containing 600 mg active ingredient, which was adjusted to pH 2.1 with 15% wt phosphoric acid under stirring. The precipitate was settled for 4 hours. The balance of the process was completed as described in Example 2, resulting in the isolation of 548 mg mevinolin with an active ingredient content of 99.7% by high pressure liquid chromatography with a dihydromevinolin content of 0.15% by gas chromatography.

$[\alpha]25_D=+329°$ (c=0.5; acetonitrile)

EXAMPLE 4

800 g of fermentation liquor cultured by the Aspergillus strain of Example 1 containing a total amount of 575 mg of mevinolin both as lactone and as hydroxy acid were diluted to 1200 g with water. Then 2.4 g ethylene glycol were added to the mixture, and the pH was maintained at 9 to 9.5 by adding 20% wt KOH solution under continuous stirring for 2 hours. The biomass was then filtered off and suspended in 400 cm³ water. The suspension was adjusted to pH 9–9.5 with 20% wt KOH solution, filtered again and the filtrates were combined. 1480 cm³ of filtered liquor containing 567 mg of active ingredient were obtained. Then 3.5 g of $CaCl_2$ were added to the liquor and the solution was adjusted to pH 2.1 with 15% wt sulfuric acid solution under stirring. The separated precipitate was settled for 4 hours and processing was completed as in Example 2, with the difference that the active ingredient was dissolved from the precipitate with 120 cm³ of isobutyl acetate recovering 527 mg mevinolin with an active ingredient content of 99.2% by high pressure liquid chromatography, containing 0.25% dihydromevinolin by gas chromatography.

$[\alpha]25_D=+329°$ (c=0.5; acetonitrile)

EXAMPLE 5

10,000 g of fermentation liquor cultured by the Aspergillus strain of Example 1 containing a total amount of 4180 mg of mevinolin both as lactone and as hydroxy acid were diluted to 15,000 g with water. Then 30 g of ethylene glycol were added to the mixture, and kept at pH 8–8.5 by adding 20% wt KOH solution under continuous stirring for 2 hours. The biomass was then filtered off and suspended in 5 dm³ water containing 10 g ethylene glycol. The suspension was adjusted to pH 8–8.5 with 20% wt KOH solution, filtered again and the filtrates were combined. Thus 18,200 cm³ of filtered liquor containing 4,091 mg of active ingredient were obtained. Then 20 g magnesium sulfate were added to the mixture and it was adjusted to pH 2.1 with 15% wt sulfuric acid solution, under stirring. The separated precipitate was settled, filtered, suspended in 1,200 cm³ of an aqueous sulfuric acid solution, adjusted to pH 2 and filtered again. The filtered aqueous precipitate was dissolved in 600 cm³ of isobutyl acetate, the aqueous phase was separated and the solvent phase was concentrated to 30 cm³. The concentrate was dissolved in 400 cm³ of isobutyl acetate, washed twice with 400 cm³ each of 2.5% wt. ammonium sulfate solution adjusted to pH 8.5 with ammonium hydroxide solution, and clarified with 6 g activated carbon by stirring for half and hour at room temperature. The solution was concentrated to 80 cm³, allowed to crystallize for 24 hours at 5° C., filtered and dried under vacuum. The balance of the process was coupled as specified in Example 2, recovering 3432 mg mevinolin with an active ingredient content of 99.1% by high pressure liquid chromatography, containing 0.19% dihydromevinolin by gas chromatography.

$[\alpha]25_D=+328.9°$ (c=0.5; acetonitrile)

EXAMPLE 6

100 kg of fermentation liquor cultured by the Aspergillus strain of Example 1 containing a total amount of 44.3 g of mevinolin both as lactone and as hydroxy acid were diluted to 150 kg with water. Then 300 g ethylene glycol were added to the mixture which was kept at pH 8.5–9 by adding 20% wt. KOH solution under continuous stirring for 2 hours. The biomass was then filtered off and suspended in 50 kg water containing 100 g of ethylene glycol. The suspension was adjusted to pH 8.5–9 with a 20% wt KOH solution, filtered off again and the filtrates were combined. 183 kg filtered liquor containing 42.9 active ingredient were obtained.

Then 200 g of magnesium sulfate were added to the liquor and the solution was adjusted to pH 2.1 with 15% wt sulfuric acid solution under stirring. The separated precipitate was settled, filtered, suspended in 12 dm³ sulfuric acid solution adjusted to pH 2, and filtered again. The filtered aqueous precipitate was dissolved in 6 dm³ isobutyl acetate, the aqueous phase was separated, and the solvent phase was concentrated to 300 cm³. The concentrate was dissolved in 4 dm³ isobutyl acetate, washed twice with 4 dm³ each of 2.5% wt. ammonium sulfate solution adjusted to pH 8.5 with ammonium hydroxide solution, and clarified with 60 g activated carbon by stirring for half an hour at room temperature. The solution was concentrated to 0.8 dm³, allowed to crystallize for 24 hours at 5° C., filtered and dried under vacuum, and the process was concluded as in Example 2, recovering 37.03 g mevinolin, having an active ingredient content of 99.3% by high pressure liquid chromatography and containing 0.18% dihydromevinolin by gas chromatography.

$[\alpha]25_D=+329.5°$ (c=0.5; acetonitrile)

EXAMPLE 7

800 g fermentation liquor cultured by an *Aspergillus terreus* strain (deposition access No. ATTC 20542) containing a total amount of 630 mg of mevinolin both as lactone and as hydroxy acid were diluted to 1,200 g. with water. Then 2.4 g ethylene glycol were added to the mixture, and the pH was maintained at 9 to 9.5 by adding 20% wt. KOH solution under continuous stirring for 2 hours. The biomass was then filtered off and suspended in 400 cm³ water. The suspension was adjusted to pH 9–9.5 with 20% wt. KOH solution, filtered again and the filtrates were combined. 1,480 cm³ of filtered liquor containing 554 mg of active ingredient were obtained. Then 3.5 g of $CaCl_2$ were added to the liquor and the solution was adjusted to pH 2.1 with 15% wt. sulfuric acid solution under stirring. The separate precipitate was settled for 4 hours and processing was completed as in Example 2, with the difference that the active ingredient was dissolved from the precipitate with 120 cm³ of isobutylacetate. 370 mg product was obtained. The obtained mevinolin has an active ingredient content of 98% by high pressure liquid chromatography, containing 0.2% dihydromevinolin by HPLC.

$[\alpha]25_D7=+326°$ C. (c=0.5; acetonitrile).

EXAMPLE 8

800 g of fermentation liquor cultured by an *Aspergillus terreus* strain and containing a total amount of 620 mg of mevinolin, both as a lactone and as hydroxy acid were diluted to 1200 g with water. Then 2.4 ethylene glycol were added to the mixture, and the pH was maintained at 8.5 to 9.0 by adding 20% wt. KOH solution under continuous stirring for 2 hours. The biomass was then filtered off and suspended in 400 cm³ water containing 0.8 g of ethylene glycol. The suspension was adjusted to pH 8.5–9. 0 with 20% wt. KOH solution, filtered again and the filtrates were combined. 1,470 cm³ of filtered liquor containing 535 mg of the active ingredient were obtained which was adjusted to pH 3.0 with 15% wt. phosphoric acid under stirring. The precipitate was settled over 4 hours. The balance of the process was completed as described in Example 2, resulting in the isolation of 334 mg mevinolin with an active ingredient content of 98.6% by high pressure liquid chromatography, with a dihydromevinolin content of 0.2% by HPLC.

$[\alpha]25_D7=+328°$ C. (c=0.5; acetonitrile).

We claim:
1. In a process for preparing mevinolin by fermentation of a culture medium, which includes dissolving mevinolin formed into the culture medium obtained by cultivation of at least one of an *Aspergillus terreus* and *Aspergillus obscurus* strain, and separating the strain from the culture medium to obtain a separated culture medium, separating the mevinolin from the separated culture medium, and recovering the mevinolin product, the improvement which consists essentially of carrying out the dissolving at a pH between about 8 and 9, and carrying out the separating of the mevinolin at a pH of between 4.5 and 2.

2. The process of claim 1, wherein the separating of the mevinolin is carried out at a pH between about 2.2 and 2.

* * * * *